United States Patent
Rath et al.

[11] Patent Number: 5,972,322
[45] Date of Patent: Oct. 26, 1999

[54] SYSTEM FOR CUSTOMIZED HAIR PRODUCTS

[75] Inventors: Maureen L. Rath; Wallace R. Hlavac, both of Minneapolis, Minn.

[73] Assignee: Tiro Industries Incorporated, Minneapolis, Minn.

[21] Appl. No.: 09/304,246

[22] Filed: May 3, 1999

Related U.S. Application Data

[63] Continuation of application No. 08/969,492, Nov. 13, 1997.

[51] Int. Cl.$^6$ .............................. A61K 7/075; A61K 7/06
[52] U.S. Cl. .................................... 424/70.11; 424/70.17; 424/70.19; 424/70.27; 424/70.28
[58] Field of Search .............................. 424/70.11, 70.17, 424/70.28, 70.19, 70.27

[56] References Cited

U.S. PATENT DOCUMENTS

| | | | |
|---|---|---|---|
| 3,577,528 | 5/1971 | McDonough et al. | 424/70.28 |
| 4,099,912 | 7/1978 | Ehrlich | 8/137 |
| 4,365,853 | 12/1982 | Ehrlich | 312/42 |
| 5,045,308 | 9/1991 | Spiegel et al. | 424/61 |
| 5,077,042 | 12/1991 | Darkwa et al. | 424/71 |
| 5,084,270 | 1/1992 | Ciaudelli | 424/59 |
| 5,108,751 | 4/1992 | Hagan et al. | 424/401 |
| 5,132,107 | 7/1992 | Lange | 424/70 |
| 5,196,187 | 3/1993 | Nicoll et al. | 424/70 |
| 5,227,503 | 7/1993 | Hagan et al. | 554/219 |
| 5,254,343 | 10/1993 | Parah et al. | 424/401 |
| 5,293,885 | 3/1994 | Darkwa et al. | 132/209 |
| 5,376,146 | 12/1994 | Casperson et al. | 8/408 |
| 5,824,295 | 10/1998 | Syed et al. | 424/70.4 |

FOREIGN PATENT DOCUMENTS

WO 97/25963   7/1997   WIPO.

*Primary Examiner*—Thurman K. Page
*Assistant Examiner*—Alysia Berman
*Attorney, Agent, or Firm*—Merchant & Gould P.C.

[57] ABSTRACT

The invention provides a system for preparing a hair shampoo, conditioner, and styling composition, wherein each system is composed of separate components that can be combined as desired by the user to provide customized hair care formulations. The systems include a water-thin base composition, a thickening composition, and optional enhancing additives, wherein each composition is separately packaged. The viscosity of the end-product shampoo, conditioner, or styling composition can be varied, from a thick, pourable liquid to a thicker, pasty material depending on the amount of thickener that is added to the base.

12 Claims, No Drawings

SYSTEM FOR CUSTOMIZED HAIR PRODUCTS

This application is a Continuation of application Ser. No. 08/969,492, filed Nov. 13, 1997, which application is incorporated herein by reference.

BACKGROUND OF THE INVENTION

Many shampoos, conditioners, styling compositions, and other hair care products that are currently available are provided as prepared formulations. A drawback of such products is that the user cannot alter the formulation to accommodate their particular hair characteristics or to provide specialized treatment.

Two- or multiple-part product kits that contain separate solutions of a shampoo, conditioner or other hair care product are available from many professional salons and some retail personal care outlets. However, the user is still unable to customize the individual formulations in light of the user's unique hair care requirements.

Therefore, one objective of the invention is to provide a system which enables a user to formulate a variety of shampoos, hair conditioners or styling compositions to best suit the hair care needs of the user. Another objective is to provide a system that is easy to use such that a cosmetologist or lay-person is able formulate a customized hair care product.

SUMMARY OF THE INVENTION

These and other objects are achieved by the present invention directed towards a hair care system for preparing shampoos, conditioners, and/or styling agents. The hair care system includes a first package containing a low-viscosity aqueous base composition and a second package containing a compatible liquid thickening composition. The thickening composition is combined with the base composition to form the hair care product having a viscosity greater than the viscosity of the base composition and/or the thickening composition.

The hair care system may include a multi-component shampoo system that includes a low viscosity shampoo base, a shampoo thickener and, optionally, one or more enhancing additives. Each component is separately packaged. The low viscosity shampoo base includes an anionic or nonionic surfactant and a major amount of water. The shampoo base is capable of being combined with varying amounts of a compatible shampoo thickener to produce a shampoo. The amount of shampoo thickener added depends on the desired viscosity of the shampoo.

The invention is also directed to a multi-component conditioner system that includes a low viscosity conditioner base, a conditioner thickener and, optionally, one or more enhancing additives. Each component is separately packaged. The low viscosity conditioner base includes a quaternary ammonium salt as an active detangling compound and a major amount of water. The conditioner base is combined with a conditioner thickener that is compatible with the conditioner base to form a conditioner with the desired consistency. The viscosity of the end-product conditioner can be varied, from a thick, but pourable liquid, to a thick paste, depending on the amount of thickener added to the base.

The invention is also directed to a multi-component hair styling system which includes a low viscosity styling base, a styling thickener and, optionally, one or more enhancing additives wherein each component is separately packaged. The styling base includes fixative agents and quaternary conditioning agents to give styling manageability and conditioning to hair. The viscosity of the end-product styling gel can be varied, from a pourable gel, to a thick, non-pourable gel, depending on the amount of thickener added to the base. Preferably, the conditioner thickening complex, described above, is also compatible with the styling base such that the conditioner thickening complex can be combined with the styling base to provide a styling cream with additional conditioning properties.

To provide a uniform distribution of ingredients in the end-product shampoo, conditioner, or styling composition, the appropriate thickening complex is added after the base and desired additives have been combined to form a homogenous mixture. Once the base and thickening composition are combined, the viscosity of the composition is substantially increased due to the chemical interaction of the ingredients. The resulting hair care product is therefore substantially thicker than either the base or thickening composition. Initially, the viscosity of the resulting composition increases as a function of time. Once the desired viscosity is obtained, it is maintained indefinitely. Typically, within about 30–60 minutes after combining the base and thickening composition, the shampoo, conditioner, or styling composition are ready to use.

Additional compositions can optionally be included in the shampoo, conditioner, or styling system to enhance hair treatment. Such compositions include shine enhancers, moisturizers, herbal additives, hair strengtheners, vitamin additives, colorants, hair thickening agents, setting and styling agents, dandruff control agents, ultraviolet absorbers, essential oils, and fragrances.

The hair care system of the invention is particularly useful in hair salons, where a hair technician can examine a client's hair and provide a customized shampoo, conditioner or styling composition that is specially formulated for that individual's hair. The hair care systems make it easy to formulate customized hair products by a hair technician or other user. Additionally, the system provides flexibility wherein some or all of the customized compositions may be changed in response to seasonal fluctuations in hair condition as well as hair style changes.

DETAILED DESCRIPTION OF THE INVENTION

The invention is directed to a system for formulating customized hair care products, such as hair shampoo, conditioner, and styling compositions. The hair care system is composed of separately packaged components, including a low-viscosity aqueous base composition, a compatible thickening composition and, optionally, one or more enhancing additives. When the thickening composition is combined with the base composition to form the customized hair care product, the thickening composition substantially increases the viscosity of the base composition.

Hair Shampoo System

The shampoo system is composed of separately packaged components including a shampoo base, a shampoo thickener and, optionally, hair enhancing additives. The individual components of the system can be combined by the user to formulate a customized shampoo end-product.

Shampoo base.

The shampoo base is a low viscosity solution which includes an anionic or nonionic surfactant. The viscosity of the shampoo base is preferably low enough such that additive ingredients are easily combined with the shampoo base. Typically the shampoo base has a viscosity from about 600 to 800 cps.

The shampoo base includes a mild detergent to effectively clean hair without damaging or stripping it. The low viscosity shampoo base is combined with a thickening agent and, optionally, one or more hair enhancing additives.

The shampoo base contains a major amount of water and is a clear to opaque. As used herein, "a major amount of water" means that the shampoo base is made of no less than 50% water. Preferably the shampoo base contains about 60–75 wt-% water. The active detergent agent of the shampoo includes an anionic, nonionic, amphoteric or zwitterionic surfactant. A preferred detergent agent includes an anionic surfactant such as sodium lauroyl sarcosinate or N-lauroyl sarcosine. The shampoo base preferably contains about 5–12% wt-% anionic surfactant, more preferably about 8–10 wt-%.

The shampoo base can also include a specialized nonionic surfactant which can function as a foam stabilizer, viscosity control agent, or a conditioning agent. Where included, the shampoo base preferably contains about 0.5–5.0 wt-% nonionic surfactant, more preferably about 0.75–2.00 wt-%.

Useful nonionic surfactants include a carboxylic amide nonionic surfactant which is a condensation product of fatty acids and hydroxyalkyl amines, such as mono- and dialkanolamides of $C_8$–$C_{22}$ fatty acids. An example is mono- or di($C_8$–$C_{22}$)alkanolamide. Commercially available, specialized nonionic surfactants suitable for use in the shampoo base include stearamide DEA, lauramide DEA, stearamide MEA, lauramide MEA, lauramide MIPA, myristamide MEA, myristamide MIPA, myristamide DEA, oleamide DEA, oleamide MEA, oleamide MIPA, cocamide DEA, cocamide MIPA, cocamide MEA, and other dialkanolamine and monoalkanolamine condensates.

Also useful are organic esters that function as nonionic surfactants and emollient esters. These include polyoxyethylene glycol($C_7$–$C_{20}$) fatty acid, esters of glycerol, such as PEG-7 glyceryl cocoate, PEG-30 glyceryl cocoate, PEG-12 glyceryl laureate, and PEG-20 glyceryl oleate.

Another useful nonionic surfactant is a polyoxyethylene glycol (PEG) ether of the diester of methyl glucose and a fatty acid. Examples of such PEG compounds include PEG-120 methyl glucose dioleate, PEG-20 methyl glucose distearate, PEG-80 methyl glucose laureate, and PEG-20 methyl glucose sesquistearate.

The shampoo base can also include a cationic polymer, such as quaternary ammonium salt, to provide substantive conditioning, detangling and improved wet and dry compatibility. Examples of useful quaternary ammonium salts include polymeric quaternary ammonium salts, also referred to as "polyquaterniums" (i.e., -6, -7, -10, -11, -16), cetrimonium chloride and steartrimonium chloride. The shampoo base can include about 0.2–2.0 wt-%, preferably about 0.5–1.0 wt-%, of a quaternary ammonium salt.

Other additives can be included in the shampoo base in lesser, but effective, amounts. Useful additives include a chelating or sequestering agent such as disodium EDTA, tetrasodium EDTA, citric acid or lactic acid. A chelating or sequestering agent is typically added to stabilize the composition. Preferably about 0.001–0.75 wt-%, more preferably about 0.03–0.25 wt-%, is added to the shampoo base. Other additives include germicidal preservative agents such as methylchloroisothiazolinone, methylisothiazolinone, phenoxyethanol, esters of parabenzoic acid, diazolidinyl urea, and imidazolidinyl urea. Preferably, the preservative is added in an effective germicidal amount, typically about 0.05–1.25 wt-%. Other additives include an antioxidant such as ascorbic acid or BHA to inhibit deterioration, typically included at about 0.001–0.5 wt-%. An appropriate amount of natural or synthetic fragrance can also be added for aesthetic purposes. An opacifying agent such as glycol. stearate or glycol distearate can be included at about 0.5–1.25 wt-% to give the shampoo an opaque or pearlescent appearance.

The shampoo base typically includes about 60–75 wt-% water, about 5–12 wt-% anionic surfactant, about 1–10 wt-% nonionic surfactant, about 0.2–2.0 wt-% of a quaternary ammonium salt and about 0.5–2.0 wt-% of an amphoteric or zwitterionic surfactant. Optionally, the shampoo base includes minor, but effective, amounts of a germicidal preservative agent, sequestering agent, antioxidant, or fragrance.

Shampoo thickening complex.

The shampoo is combined with an anionic or nonionic shampoo thickening complex to convert the low-viscosity shampoo base to the thickened end product shampoo. The shampoo thickening complex combines with elements present in the shampoo base to form micelles. The micelles swell, which results in thickening of the end product shampoo. To facilitate mixing, the shampoo thickening complex preferably has a low viscosity such that it is easily combined with the low viscosity base. Typically, the shampoo thickening complex has a viscosity from about 500 to 1000 cps. Preferably, the shampoo thickener contains an amphoteric or zwitterionic surfactant such as cetyl betaine in a 20–25 wt-% active aqueous solution.

The shampoo thickener is compatible with the shampoo base. As used herein "compatible" means that the thickener is miscible with the base. The thickener does not coagulate or precipitate upon being combined with the base. Instead, the thickener and base are easily combined to form a stable solution. Combining the shampoo thickener with the shampoo base results in an end-product shampoo with a viscosity greater than the shampoo base or shampoo thickener.

Preferably the shampoo thickener is added to the base after the desired enhancing additives have been combined with the shampoo base to form a homogeneous mixture. The thickness, or viscosity, of the product shampoo can be controlled by the amount of thickener added to the shampoo base. Therefore, the end-product shampoo can be formulated over a broad range of viscosities, from a creamy, but pourable liquid to a dense, gelled or paste-like material.

For example, the addition of about 2–3 parts thickener to about 97–98 parts shampoo base provides an end-product shampoo with a viscosity of about 1500 cps–3000 cps within about 10–15 minutes. Combining 4–6 parts thickener to 94–96 parts shampoo base produces an end-product shampoo with viscosity of about 4000 cps–7000 cps within about 10–15 minutes after the thickener is added. Although the viscosity of the end-product shampoo initially increases as a function of time, once the desired viscosity is obtained, that viscosity will be maintained indefinitely.

A preferred shampoo formulation includes about 100 parts shampoo base combined with about 1–7 parts colorant composition, about 0.25–0.5 parts shine enhancing additive, about 0.25–1.0 parts moisturizing composition, about 1–5 parts herbal additive, about 0.5–1.0 parts hair strengthening composition, and about 0.5–2.0 parts vitamin additive. The shampoo base is thoroughly mixed with the additive compositions, and then combined with about 3–5 parts of shampoo thickening complex depending on the desired viscosity. For example, the addition of about 3 parts shampoo thickener results in a shampoo with a viscosity of a thin, pourable liquid. In contrast, the addition of about 5 parts shampoo thickener results in a shampoo with a viscosity of a pourable, moderate viscosity liquid.

Shampoo enhancing additives.

The shampoo system can optionally include one or more additives to enhance hair treatment. The additives may be packaged individually or as a blend containing multiple, complimentary additives. To ensure an even distribution of ingredients in the end-product shampoo, the shampoo enhancing additives are preferably added to the low viscosity shampoo base prior to addition of the shampoo thickener.

An example of a useful enhancing additive includes a hair strengthening composition. Suitable hair strengthening compositions include plant or animal proteins such as wheat protein or collagen. Other enhancing additives include herbal compositions that contain plant extracts such as aloe, to provide a soothing effect, or cucumber, to provide a stimulating effect. A shine enhancer made of organosiloxanes or silicone polymers can also be included along with moisturizing compositions containing plant-, animal-, or mineral-based oil. Additionally, vitamins, colorants or fixative compositions, such as those containing resins and quaternary ammonium salts to provide styling control and conditioning, can be added.

Hair Conditioner System

The hair conditioner system provides a customized composition that is applied to wet hair after shampooing. The hair conditioner includes cationic ingredients to make hair soft and combable, and to provide antistatic effects, sheen, manageability and detangling.

The conditioner system includes a conditioner base, a conditioner thickener, and optional hair enhancing additives. The conditioner base has a low viscosity, similar to that of water, such that additive ingredients are easily combined with the conditioner base. Typically, the conditioner base has a viscosity less than about 25 cps.

When the conditioner base is combined with a conditioner thickener, the viscosity of the conditioner base is substantially increased due to chemical interactions between the ingredients. The resulting end-product conditioning composition is therefore substantially thicker than either the base or thickening composition.

Conditioner base.

The conditioner base is prepared as an aqueous, low viscosity solution. The viscosity of the conditioner base is typically less than about 25 cps. Typically the conditioner base is clear to opaque and contains a concentrated mixture of cationic detangling ingredients. Sorption of the cationic detangling ingredients onto hair helps reduce the resistance of wet hair to combing, improves feel and texture, and reduces static charge. The cationic detangling ingredient preferably includes a water-soluble quaternary ammonium compound. Examples of useful quaternary ammonium compounds include cetrimonium chloride, steartrimonium chloride, and polyquaternium (i.e., -6, -7, -10, -11, -16). The quaternary ammonium compound is preferably included in the conditioner base at about 0.2–1.5 wt-%, more preferably about 0.5–1.0 wt-%.

Preferably, the conditioner base also includes an emulsifying agent to provide a uniform dispersion or emulsion of water-insoluble emollients. Typically the conditioner base contains about 0.5–1.5 wt-% of an emulsifying agent. A useful solubilizer is a polyalkylene glycol ether of a $C_{12}$–$C_{18}$ fatty alcohol such as isoceteth-20, oleth-10, oleth-20, laureth-23, polysorbate-80, polysorbate 20, or nonoxynol-10.

The emulsifier can also be supplemented with a polyhydric alcohol such as propylene glycol, glycerol, sorbitol or other $C_2$–$C_5$ alkanols substituted with 2–4 hydroxyl groups; or a $C_6$–$C_{12}$ acid diester of propylene glycol such as propylene glycol dicaprylate, propylene glycol dicaprate, mixtures thereof, or a mixed caprate/caprylate ester.

The conditioner base can also include other additives such as a germicidal preservative agent. Methylparaben, propylparaben, sodium hydroxymethyl glycinate, and diazolidinyl urea are examples of preservative agents that can be included in an effective germicidal amount, preferably about 0.05–1.25 wt-%. A minor amount of a natural or synthetic fragrance can also be added for aesthetic purposes, preferably about 0.01–1.0 wt-%. A chelating or sequestering agent such as disodium EDTA or citric acid can be included to stabilize the composition, typically in an amount of about 0.001–0.5 wt-%. An antioxidant such as ascorbic acid or BHA can be included at about 0.001–0.5 wt-% to inhibit deterioration of the conditioner base.

A typical conditioner base contains about 90–99 wt-% water, more preferably about 94–96 wt-%. Additionally, the conditioner base contains about 0.2–1.5 wt-% quaternary ammonium compound, about 0.75–1.25 wt-% emulsifier, and about 0.05–1.25 wt-% of a germicidal preservative agent. Optionally, the conditioner base includes minor amount of fragrance. As used herein, "a minor amount of fragrance" means that the composition contains less than about 0.5% fragrance.

Conditioner thickening complex.

To transform the conditioner base into an end-product conditioner with a suitable viscosity, the hair conditioner system includes a thickening complex that is mixed with the hair conditioner base solution. The thickener is typically water-dispersible, oil-based, cationic, polymeric solution with a viscosity from about 100 to 250 cps. The conditioner thickening complex contains a quaternary ammonium salt in an emulsifying agent or emollient oil.

The conditioner thickening complex is compatible with the conditioner base. As used herein "compatible" means that the conditioner thickening complex is miscible with the conditioner base. The thickening complex does not coagulate or precipitate upon being combined with the conditioner base. Instead, the thickener and base are easily combined to form a stable solution. The conditioner thickener functions as a polymeric dispersion which, upon being blended with the conditioner base, swells to uniformly thicken the conditioner base to form a stable, custom designed end-product conditioner. A preferred thickening agent is Salcare SC-96 liquid dispersion polymer (available from Allied Colloids; Suffolk, Va.). Salcare SC-96 contains polyquaternium-37, propylene glycol dicaprylate/dicaprate, PPG-1 and trideceth-6 and is typically supplied as a small particle dispersion of hydrophilic polymer in a high purity ester solvent carrier.

Upon addition to aqueous systems, the hydrocarbon carrier oil is converted to an oil-in-water emulsion. At the same time, the hydrophilic polymer is exposed to water, which results in a smooth and rapid development of viscosity.

The conditioner thickening complex is preferably combined with the conditioner base after the addition and dispersion of the other desired ingredients to insure an even distribution of ingredients in the composition. The viscosity of the conditioner can be varied, from a pourable liquid to a relatively stiff viscous cream, depending on the amount of conditioner thickening complex added. When the thickening complex is added to and mixed with the conditioner base solution, the thickener swells, causing the end-product conditioner to uniformly thicken to a viscosity greater than either the conditioner base or the conditioner thickener.

For example, a conditioner formulated with about 1.5–3 parts conditioner thickener to about 97–98.5 parts conditioner base, typically achieves a maximum viscosity of about 10,000–50,000 cps within about 1–2 hours following the addition of the thickener to the base. The conditioner maintains that thickness indefinitely. By comparison, a conditioner formulated with about 4–5 parts thickener to about 95–96 parts base typically achieves a maximum viscosity of about 100,000–150,000 cps within about 1–2 hours. The conditioner maintains that thickness indefinitely.

The conditioner is preferably formulated with about 100 parts conditioner base to which is added about 1–7 parts colorant composition, about 3–5 parts shine enhancing additive, about 3–5 parts moisturizing composition, about 1–5 parts herbal additive, about 3–10 parts hair strengthening composition, and about 1–5 parts vitamin additive. After thoroughly mixing the conditioner base with the additive compositions, about 2–5 parts of the thickening complex is added, depending on the desired viscosity. For example, adding about 2 parts of thickener provides a "light" conditioner with a viscosity of a pourable liquid. Adding about 5 parts thickener provides a "heavy" conditioner with a viscosity of a stiff cream. Styling or volumizing compositions can be added to the conditioning base, before thickening, to create a leave-in styling cream. Additionally, the styling composition thickener can be used to thicken the conditioner for a different consistency conditioner. The same ratios of base to thickening agent still apply.

Conditioner enhancing additives.

The conditioner system can additionally include one or more compositions to enhance hair treatment. To insure an even distribution of enhancing additives in the end-product, the conditioner enhancing additives are preferably added to the conditioner base prior to addition of the conditioner thickener.

Examples of useful enhancing additive include hair strengthening compositions or herbal compositions containing plant extracts such as aloe, to provide a soothing effect, or cucumber, to provide a stimulating effect. A shine enhancer made of organosiloxanes or silicone polymers can also be included along with moisturizing compositions. Additionally, vitamins, colorants, fixative compositions, or moisturizing compositions can be added. Examples of suitable moisturizing compositions include oil-based moisturizing compositions such as plant or animal oils.

Hair Styling System

The multi-component hair styling system includes a low viscosity styling base, a styling thickener, and, optionally, one or more enhancing additives wherein the components are separately packaged.

Styling base.

The styling base is prepared as a low viscosity, aqueous solution. The viscosity of the styling base is preferably low enough that additive ingredients are easily combined with the base. Typically, the styling base has a viscosity from about 200 to 600 cps. The styling base preferably contains fixative agents and quaternary conditioning agents to provide styling manageability (hold) and conditioning.

A fixative agent is included in the styling base. The fixative agent forms a film on the user's hair that helps hold the hair in a given style. Examples of suitable fixative agents include polyvinyl pyrrolidone (PVP), a copolymer of polyvinyl pyrrolidone and polyvinyl alcohol (PVP/VA), a copolymer of polyvinyl pyrrolidone and hexadecene, butylated polyvinyl pyrrolidone, a copolymer of polyvinyl pyrrolidone and dimethylaminoethylmethacrylate, a butyl ester of a polymethylvinylether and maleic anhydride copolymer (PVM/MA), or an ethyl ester of PVM/MA. The styling base can include about 2 wt % to about 8 wt % of a fixative agent, more preferably about 4 wt % to about 6 wt %.

Examples of suitable quaternary conditioning agents include polyquaterniums (i.e., -6, -7, -10, -11, -16, -28). The styling base can include about 0.25 wt % to about 4.00 wt %, preferably about 0.5 wt % to about 1.0 wt %, of a quaternary ammonium salt.

Typically, the styling base includes about 85–90 wt % water, more preferably about 90–92 wt % water. Additionally, the styling base includes about 2 wt % to about 4 wt % fixative agent, about 0.5 wt % to about 1.0 wt % quaternary conditioning agent, 0.03–0.25 wt % chelating agents/sequestering agents such as disodium EDTA or tetrasodium EDTA, and 0.05–2.0 wt % humectant such as glycerin, propylene glycol, or sorbitol. Optionally, the styling base includes about 0.05 wt % to about 1.25 wt % of a germicidal preservative agent such as methylparaben, propylparaben, diazolidinyl urea, or phenoxyethanol.

Styling Thickening agent.

To transform the low-viscosity styling base into a styling composition with a suitable viscosity, the styling system includes a water dispersible thickening agent that is compatible with the styling base. As used herein "compatible" means that the thickening agent is miscible with the styling base. Thus, the thickening agent does not coagulate or precipitate upon being combined with the base. Instead, the thickening agent and base are easily combined to form a stable solution.

The thickening complex functions as a polymeric dispersion, which, upon being blended with the styling base, swells to produce an end-product styling composition having a viscosity greater than either the styling base or the styling thickening complex. A preferred styling thickening agent is a translucent, pourable, water-dispersible liquid. Preferably the thickening agent contains polyacrylamide, C13–14 isoparaffin and laureth-7. An example of a suitable thickening agent is Sepigel 305 (available from Seppic, Inc.; Fairfield, N.J.).

The viscosity of the end-product styling gel can be varied from that of a pourable gel, to a thick, non-pourable gel, depending on the amount of thickener added to the base. The styling thickening complex is preferably combined with the styling base after the addition and dispersion of the other desired ingredients to insure an even distribution of ingredients in the composition.

After the styling thickener is added to the styling base, the mixture is shaken for 2–5 minutes, after which the mixture is allowed to rest for 15–30 minutes. After 15–30 minutes, the mixture is shaken again. At this time, the viscosity of the styling product is about 75% of the final viscosity. The final viscosity typically develops after 12–24 hours.

For example, adding about 1 to 2 parts thickener to about 98 to 99 parts styling base provides an end-product styling gel with a viscosity of about 5000 to 10,000 cps within about 1 to 2 minutes. The end-product styling gel becomes thicker over time, reaching a maximum viscosity of about 12,000 to 15,000 cps after about 12–24 hours. The composition retains that viscosity indefinitely.

The styling gel is preferably formulated with about 100 parts styling base to which is added about 1–5 parts herbal additive, 0.1–0.2 parts shine additive, 0.5–1.0 parts hair strengthening additive and 1–5 parts vitamin additive. If additional hold is desired, 1–5 parts volumizing/styling composition are added. After thoroughly mixing the conditioner base with the additive compositions, the hair styling thickening complex is added at about 1–4 parts, according to the desired amount of thickness. For example, the addition of about 1–2 parts thickener with provide a "light" gel with the viscosity of a pourable liquid (5,000–10,000 cps), and the addition of about 3–4 parts thickener will provide a "heavy" gel with a viscosity of a stiff gel (100,000–200,000 cps).

Optionally, the conditioner thickener, discussed above, can be added to the styling base, in place of, or in addition to the styling thickener, to enhance the conditioning properties of the gel composition.

Styling enhancing additives.

The styling system can additionally include one or more compositions to enhance hair treatment. To insure an even distribution of enhancing additives in the end-product, the styling enhancing additives are preferably added to the styling base prior to addition of the styling thickener.

Examples of useful enhancing additives include a hair strengthening composition or herbal compositions containing plant extracts. A shine enhancer can also be included along with moisturizing compositions. Additionally, vitamins or colorants can be added. For additional hold, a volumizing/styling composition can be added.

Enhancing Additives

The shampoo, hair conditioner, and styling systems may optionally include one or more compositions for enhancing properties of the system. Examples of suitable enhancing additives include a shine enhancer, oil-based moisturizer, herbal additive, hair strengthener, vitamin additive, colorant, body building and conditioning polymers, natural or synthetic fragrance oils (aroma), UV absorbers, and dandruff control compounds.

Shine enhancer.

A shine enhancer provides sheen, gloss and smoothness to hair and leaves a silky, lustrous feel. Additionally, a shine enhancer facilitates wet and dry combing and reduces fly-away tendencies. Typically, a shine enhancer composition is formulated as a concentrated liquid mixture of silicone compounds.

Useful silicone compounds (organosiloxanes) include cyclomethicone, dimethicone, dimethiconol, dimethicone copolyol, polydimethylsiloxane, and phenyltrimethicone.

Oil-based moisturizer composition.

A moisturizer composition can also be included in either the shampoo or hair conditioner system to provide emolliency and moisture or to help nourish and enhance the vibrancy of dull, dry or damaged hair. A moisturizer composition typically includes a flowable animal-, plant- or inorganic oil that forms a thin-film coating on hair fibers. A preferred moisturizer composition includes of about 75–85 wt-% oil, and about 15–25 wt-% solubilizing agent.

Useful plant-derived oils include rice bran oil, meadow-foam oil, evening primrose oil, olive oil, copaiba oil, aloe vera oil, soybean oil, persic oil (apricot or peach kernel oil), corn oil, coconut oil, safflower oil, cottonseed oil, peanut oil and sesame oil. Plant-derived oils can be obtained by cold pressing or extraction with alcohol or hydrocarbon solvents, or from a commercial source, such as Fanning, ADM, Cargill or Jojoba Growers.

Animal-derived oils that are effective moisturizers include cod liver oil, mink oil, shark oil, sperm oil, tallow, and oleic acid derivatives.

The moisturizing oil can also be an inorganic oil such as mineral oil, petrolatum or aliphatic hydrocarbons.

The moisturizer can further include additives such as a solubilizing agent. Suitable solubilizing agents include propylene glycol or an ester thereof such as propylene glycol dicaprylate/dicaprate. Other suitable additives include vitamins, such as tocopherol acetate (vitamin E); preservatives, such as a paraben compound; antioxidants; or sequestering agents.

Herbal additive composition.

A useful composition for enhancing either the shampoo, conditioner or styling product is an herbal additive composition that includes one or more plant-derived extracts to provide either a soothing or stimulating effect. The plant extract can be derived from flowers, twigs, roots and other plant parts by methods known and used in the art. For example, an extract can be obtained using water or steam distillation or extraction using alcohol, propylene glycol, glycerin, or a hydrocarbon solvent, cold-pressing or fluid maceration. Plant extracts are also commercially available, for example, from Active Organics, Brooks Industries or Bio Botanica.

A preferred herbal composition is composed of 80–99 wt-% water, about 1–20 wt-% herbal extract, about 0.4–1 wt-% polyhydric alcohol emollient, and about 0.05–1.25 wt-% germicidal preservative agent.

A soothing herbal additive provides a tranquilizing or anesthetizing character to the shampoo or conditioner to help restore a healthy feel and glow to stressed hair or the scalp. Soothing herbal extracts include extracts of witch hazel, calendula, sunflower, aloe vera, lavender, and birch leaves.

A stimulating herbal additive composition can be included to provide naturally stimulating or astringent qualities to refresh or invigorate the hair and scalp. Examples of stimulating herbal extracts include clove, eugenol, camphor, matricaria (chamomile), cucumber, kola nut, peppermint, spearmint, wintergreen, menthol, basil, sage, eucalyptus, balsams, pine needles, citronella, creosote, capsicum, and juniper.

Volumizing/Styling Composition.

A volumizing/styling composition is a concentrated liquid mixture that provides additional styling control when used in the styling base. When used in the shampoo base, the volumizing/styling composition leaves the hair feeling thicker, fuller, and more manageable. When combined with conditioner base and conditioner thickener, a leave-in styling cream is created, giving the user light styling control with conditioning. If combined with the traditional rinse-out conditioner system, the volumizing/styling composition leaves the hair feeling thicker, fuller, and more manageable.

A volumizing/styling composition typically contains 85–90 wt % water, 5–10 wt % fixative agent, 0.5–3 wt % quaternary conditioning agents (e.g., polyquaternium-6, -7, -10, -11, -16, -28), and 0.05–1.25 wt % of a germicidal preservative agent.

Strengthening Composition.

The shampoo, conditioner or styling system can also include a strengthening composition that contains a strengthening agent to penetrate the hair to help condition, strengthen and retain moisture in fine, limp hair and protein deficient hair. The strengthening agent can also provide deep conditioning for excessively dry or chemically processed hair. A hair strengthening composition typically includes one or more plant-derived proteins, animal-derived proteins, amino acids, or a combination thereof. Preferably, the hair strengthening composition is a blend of concentrated proteins.

A preferred protein strengthening composition is composed of about 60–80 wt-% water, about 20–40 wt-% plant or animal protein, and about 0.2–0.5 wt-% of a germicidal preservative agent. Preferred germicidal agents include methylchloroisothiazolinone, methylisothiazolinone, diazolidinyl urea, imdazolidinyl urea, methylparaben, propylparaben, or phenoxyethanol.

Plant-derived proteins that are useful for providing strengthening properties include wheat protein, soybean protein, gluten, algae, plankton, hydrolyzed wheat, hydrolyzed soy protein, and derivatives thereof. Gluten protein may be derived from wheat, corn, oats, rice, and other cereal grains.

Useful animal-derived proteins include collagen, casein derived from milk, albumin derived from blood or egg, gelatin, keratin, human hair keratin, silk, other protein-containing substances and derivatives thereof. Preferred animal proteins are those that have a molecular weight of about 5000 cps–100,000 cps.

Preferred amino acids include methionine, cysteine and collagen amino acids.

Vitamin additive composition.

A vitamin source can be included in the shampoo or conditioner system to enhance hair that has become dull looking or porous, helping restore it to a healthy condition.

Examples of vitamins that can be included in a vitamin additive composition are vitamin A and analogs thereof, including retinol (vitamin $A_1$), dehydroretinol (vitamin $A_2$) and retinoic acid (vitamin A acid; tretinoin), which can be in the form of vitamin A acetate (retinol acetate), vitamin A palmitate (retinol palmitate), or vitamin A aldehyde (retinol aldehyde); vitamin C (ascorbic acid); vitamin D including cholecalciferol, calcitriol (vitamin $D_3$) and ergocalciferol (vitamin $D_2$); vitamin E, including tocopherol and tocotrienol derivatives, such as alpha tocopherol; and alcohols with vitamin activity such as panthenol (provitamin $B_5$).

The vitamin additive is preferably prepared as an aqueous solution. Other ingredients can also be included in the additive. For example, a quaternary ammonium salt such as dicetyldimonium chloride, cetrimonium chloride, stearalkonium chloride can be included to provide a vehicle for substantive sorption of the vitamin additives by the hair. A sequestering agent such as tetrasodium EDTA or citric acid can also be added. Additionally, sorbitol or other solubilizing agents for vitamins A and D or other oil-soluble vitamins are suitable additives. A nonionic surfactant such as an ethoxylated alkylphenol, for example, polyoxyethylene (9–10) nonylphenol (nonoxynol) can be added to provide solubility of additives and surface tension reduction (wetting action) on the hair. A silicone compound such as dimethicone copolyol, cyclomethicone can be added to provide moisture retention, function retention, and gloss to the hair. A germicidal agent such as diazolidinyl urea, DMDM hydantoin or parabens such as methylparaben or propylparaben are suitable additives, as are antioxidants, such as ascorbic acid, for microbial control, stability of color, fragrance and freshness.

A preferred vitamin composition is composed of about 90–99 wt-% water, preferably about 93–95 wt-%; about 0.0001–0.5 wt-% vitamins such as vitamins A, D and E; about 0.5–2 wt-% solubilizing agent, preferably sorbitol; about 1–3 wt-% quaternary ammonium salt such as dicetyl dimonium chloride and wheat germamidopropalkonium chloride; about 0.05–0.3-wt-% sequestering agents, preferably EDTA; about 0.1–0.5 wt-% nonionic surfactant; about 0.1–0.5 wt-% of a silicone compound, preferably dimethicone; and about 0.5–2 wt-% of a germicidal agent.

Colorant composition.

The systems of the invention may also include coloring agents, such as semi-permanent dyes. Adding a coloring agent to the shampoo, conditioner or styling composition enhances the appearance of color treated hair and can highlight the natural color of untreated hair.

A coloring agent can include a synthetic direct dye such as those available commercially from Whittaker, Clark & Daniels, William H. Lowenstein & Sons, Pylam, Hilton Davis.

The coloring agents can include shades of blue, black, yellow, orange, red, violet, brown. Preferred coloring agents include Disperse black 9, Lowacryl red 46, Lowadene orange 3, Basic Violet 1, Lowacryl Red 46, Lowacryl Blue 26, Lowacryl Blue 3, Lowacryl Blue 90, Lowacryl Green 4, Lowacryl Blue 7, Lowalan Blue 9, Lowacryl Brown 4, Lowacryl Orange 1, Lowacryl Violet 1, Disperse Blue 7, Disperse Blue 3, Disperse Orange 3, Acid Orange 3, Disperse Violet 1, HC Blue No. 4, HC Yellow No. 4, HC Yellow No. 5, Basic Red 2, and Basic Red 22.

A colorant composition can be included in the shampoo or conditioner as a single color tone or as a blend of one or more other shades to produce a customized tone. Test swatches of the dyes on wool or other suitable fiber substrates provide a convenient reference guide for mixing color shades.

The colorant composition is preferably formulated as a concentrate of a coloring agent in a nonionic or amphoteric surfactant system with an emollient organic ester such as a polyoxyethylene (($C_8$–$C_{12}$) fatty acid) ester of glycerol, for example, PEG-7 glyceryl cocoate or a mixed polyalkylenoxy ether such as PPG-5-ceteth-20.

Other suitable additives include a nonionic surfactant such as octoxynol; an amphoteric surfactant such as cetyl betaine; a sequestering agent such as disodium or tetrasodium EDTA or citric acid; a mold or yeast inhibitor such as potassium sorbate; or a germicidal preservative agent such as dimethyl hydroxymethyl pyrazole to provide antimicrobial activity.

A preferred colorant composition includes about 60–75 wt-% water, about 0.5–4 wt-% colorant, about 20–30 wt-% emollient oil, about 2–8 wt-% nonionic surfactant, preferably about 0.5–2.0 wt-% amphoteric surfactant such as cetyl betaine, about 0.2–0.8 wt-% penetration enhancer, and about 0.05–0.2 wt-% sequestrant.

Additives

Any or all of the compositions can optionally include a germicidal preservative agent, an antioxidant, a chelating or sequestering agent, polyhydric alcohol, a natural or synthetic fragrance, or ultraviolet absorbers.

A germicidal agent can be included as a preservative and to control bacterial, fungal, yeast, mold or other microbial growth in the composition during storage. A preferred germicidal agent is a paraben compound which is a $C_1$–$C_4$ lower alkyl- or benzyl-ester of hydroxy-benzoic acids such as methyl paraben, butyl paraben and propyl paraben. Other useful germicidal agents include diazolidinyl urea, imidazolidinyl urea, phenoxyethanol, DMDM hydantoin, benzoic acid, potassium sorbate, and sodium hydroxymethylglycinate. The germicidal agent can be included in a composition at about 0.01–2 wt-%, preferably about 0.05–0.7 wt-%.

An oil-soluble antioxidant can also be included in a composition to inhibit deterioration by oxidative processes that can result in rancidity or inactivation of ingredients. Examples of useful antioxidants include ascorbic acid, potassium metabisulfite, sodium sulfite, sodium metabisulfite, sodium bisulfite, sodium thiosulfite, ascorbyl palmitate, and alpha-tocopherol.

A sequestering agent such as ethylenediamine tetracetic acid (EDTA) derivatives or a hydroxycarboxylic acid such as citric, lactic, tartaric, gluconic or saccharic acids, can be included in a composition at about 0.001–0.5 wt-%, to stabilize or enhance the activity of an antioxidant or germicidal agent.

A polyhydric alcohol can be included as a solvent, preservative or solubilizer. Examples of useful polyhydric alcohols include propylene glycol, glycerol, sorbitol or other $C_2$–$C_5$ alkanol substituted with 2–4 hydroxyl groups. A polyhydric alcohol can be included in minor amounts, typically about 0.1–2 wt-%.

Optionally, the composition can include a natural or synthetic fragrance for cosmetic purposes. Useful fragrances include essential oils derived from flowers, stems, leaves or other plant parts that contain terpenes. The fragrances can be obtained by water or steam distillation. Examples of aromatic natural oils include jojoba, jasmine oil, rose oil, clove leave oil, mimosa, rosemary oil, sandalwood oil, cinnamon, citronella, eucalyptus, geranium, juniper, lemon, peppermint, pine, and others. Also useful are synthetic fragrances such as phenethyl alcohol (rose oil), citronellol, cinnamic acid, cinnamaldehyde, jasmal, and vanillin. UV absorbers can be added to protect hair from the harmful effects of ultraviolet light. Examples of suitable UV absorbers include Benzophenone-3, benzophenone-4, octylmethoxycinnamate, and oxybenzone.

Packaging System

The components that make up the shampoo, conditioner and styling systems are packaged separately as part of an article of manufacture, or kit.

The kit for the hair care system includes a base, a thickener and separate enhancing additives, wherein each component is packaged in a separate container such as a vial, jar, pouch, or tube. The kit further includes instructions for formulating the hair care product or using the hair care product. The instructions can provide one or more formulations of the components, including combinations of the base with the thickener and desired enhancing additives, to achieve a desired shampoo, conditioner or styling composition. The components of the kit, i.e., the base, thickener, enhancing additives and instructions can be contained or separately packaged within a packaging material, such as a box or bag.

It is preferred that the kit include a dispenser for apportioning a measured amount of thickener or enhancing additive into the shampoo, conditioner, or styling base. Examples of suitable dispensers include containers having a pump dispenser, as known and used in the art. Preferably the pump is calibrated to dispense about 0.5–15 ml of a composition each time the pump is depressed.

Formulation and Preparation of the Compositions

To prepare the hair care composition, the base, formulated with ingredients described above, is combined with the desired enhancing additives. The ingredients are typically mixed together by vigorous shaking for about 2–5 minutes or until a uniform mixture of the ingredients is achieved in the low viscosity base. A predetermined amount of thickener is then added to the low viscosity mixture, the mixture is vigorously shaken to provide a homogenous mixture and then allowed to rest. The mixture gradually becomes thicker over time. Preferably, the hair care product is vigorously shaken prior to each use.

Use of the Formulated Compositions

To use the formulated shampoo, the user's hair is wetted and the shampoo is massaged into the hair. After the shampoo is rinsed from the hair, using water, the formulated conditioner is applied and massaged into the wet hair. After about 1–2 minutes, the conditioner is rinsed out of the hair, which is then combed and dried. The styling gel/cream formulation can be applied to wet or dry hair depending on the styling needs to the user.

The invention will be further described by reference to the following detailed examples described below. These examples are not meant to limit the scope of the invention that has been set forth in the foregoing description. Variation within the concepts of the invention are apparent to those skilled in the art. The abbreviation "CTFA", used throughout the examples, refers to the designation of an ingredient given by the Cosmetic, Toiletry and Fragrance Association. The disclosures of the cited references throughout the specification are incorporated by reference herein.

EXAMPLE 1

Shampoo Base Composition

A shampoo base was prepared by combining the ingredients shown in TABLE 1 below, in the following manner:

Add water to a mixing vessel equipped with prop mixer, heating and cooling capabilities. Adjust mixing to form a vortex (300 rpm). Sprinkle polyquaternium-10 into the vortex. Mix until the powder is dispersed. Begin heating to 50–55° C. At 50–55° C., add tetrasodium EDTA. Continue heating to 70° C. Hold at 70° C. with mixing for one hour, or until clear (hydrated). Add stearamide DEA and stearamide MEA at 70° C. Mix at 70° C. for 15 minutes, or until melted and uniform. Turn off heat. Add cetyl betaine, PEG-7 glyceryl cocoate, PEG-120 methyl glucose dioleate, and sodium lauroyl sarcosinate, mixing until uniform after each addition. When uniform, begin cooling to 35° C. or lower. Reduce mixing speed to 150–200 rpm at 45–50° C. Continue cooling. At 35° C. add hydrolyzed wheat protein polysiloxane copolymer, aloe barbadensis gel, fragrance, and preservative. Mix for 15 minutes, or until uniform. Continue cooling to 25° C. Add enough citric acid to increase the viscosity to 600–800 cps at 25° C.

The composition was an opaque, white, watery liquid.

TABLE 1

| Ingredient | % | CTFA Designation |
| --- | --- | --- |
| Deionized Water | 65.70 | (Water) |
| Celquat SC-240 | 0.25 | (Polyquaternium-10) |
| Hampene 100S | 0.05 | (Tetrasodium EDTA) |
| Methylparaben | 0.20 | (Methylparaben) |
| Alkamide S280 | 1.50 | (Stearamide MEA) |
| Monamid S | 1.00 | (Stearamide MEA) |
| Detain PB | 3.00 | (Cetyl Betaine) |
| Cetiol HE | 1.50 | (PEG-7 Glyceryl Cocoate) |
| Glucamate DOE-120 | 2.00 | (PEG-120 Methyl Glucose Dioleate) |
| Hamposyl L-30 | 24.0 | (Sodium Lauroyl Sarcosinate) |
| Citric Acid | 0.50 | (Citric Acid) |
| Kathon CG | 0.05 | (Methylisothiazolinone (and) Methylchoroisothiazolinone) |
| Fragrance | 0.25 | (Fragrance) |
|  | 100% |  |

EXAMPLE 2

Shampoo Thickening Complex

The shampoo thickener was a commercially prepared cationic surfactant from DeForest, under the trade name Detaine PB. The formulation of the cationic surfactant is shown below in TABLE 2. The composition was a viscous, slightly hazy, straw colored liquid.

TABLE 2

| Ingredient | % | CTFA Designation |
|---|---|---|
| Detaine PB (DeForest) | 100 | (Cetyl Betaine, 20% active) |

EXAMPLE 3

Conditioner Base Composition

A conditioner base can be prepared by combining the ingredients shown in TABLE 3, below, and mixing the ingredients in the following manner:

Add water to a mixing vessel equipped with prop mixer. Add cetrimonium chloride, polyquaternium-7, and preservative to vessel. Mix at 200–250 rpm until uniform (15–30 minutes). Premix fragrance and isoceteth-20. Add premix to vessel. Mix at 200–250 rpm until clear and uniform (15–30 minutes).

The resulting composition is a clear, water-thin liquid.

TABLE 3

| Ingredient | % | CTFA Designation |
|---|---|---|
| Deionized Water | 94.10 | (Water) |
| Carsoquat CT429 | 2.50 | (Cetrimonium Chloride) |
| Merquat 550 | 1.00 | (Polyquaternium-7) |
| Germaben II | 1.00 | (Propylene Glycol, Diazolidinyl Urea, Methylparaben, Propylparaben) |
| Fragrance | 0.30 | (Fragrance) |
| Arlasolve 200L | 1.00 | (Isoceteth-20) |
| Suttocide A | 0.10 | (Sodium Hydroxymethylglycinate) |
| | 100% | |

EXAMPLE 4

Conditioner Thickening Complex

The conditioner thickener was a commercially prepared polymeric dispersion manufactured by Allied Colloids under the trademark SALCARE SC-96. The formulation of the SALCARE colloid material is shown below in TABLE 4. The composition was an opaque, white, slightly viscous liquid.

TABLE 4

| Ingredient | % | CTFA Designation |
|---|---|---|
| Salcare SC-96 Allied Colloids | 100% | (Polyquaternium-37, Propylene Glycol Dicaprylate/Dicaprate PPG-1 Trideceth 6) |

Additional products from Allied Colloids that can be used in this system are listed in TABLE 5, below.

TABLE 5

| Ingredient | % | CTFA Designation |
|---|---|---|
| Salcare SC-91 | 100% | (Sodium Acrylate Copolymer, Mineral Oil, PPG-1 trideceth-6) |
| Salcare SC-95 | 100% | (Polyquaternarium-37, Mineral Oil, PPG-1 Trideceth-6) |
| Salcare SC-92 | 100% | (Sodium Acrylate Copolymer, Propylene Glycol Dicaprylate Dicaprate, PPG-1 Trideceth-6) |

EXAMPLE 5

Styling Base Composition

A styling base was prepared by combining the ingredients shown in TABLE 6, below, in the following manner:

Add water to a stainless steel vessel equipped with a prop mixer. Add preservative to the water and mix for 15 minutes, or until uniform. Add PVP, polyquaternium-11 and PVP/VA copolymer solutions with mixing. Mix for 30–60 minutes, or until uniform.

The resulting product is a yellow, clear, low viscosity liquid.

TABLE 6

| Ingredient | % | CTFA Designation | Comments |
|---|---|---|---|
| Deionized Water | 88.0 | (Water) | |
| Germaben II | 1.0 | (Propylene Glycol (and) Diazolidinyl Urea (and) Methylparaben (and) Propylparaben) | |
| PVP K-90 | 2.0 | (PVP) | 20% solution in water |
| Gafquat 755N | 3.0 | (Polyquaternium-11) | 20% solution in water |
| PVP/VA W-735 | 6.0 | (PVP/VA Copolymer) | 50% solution in water |

EXAMPLE 6

Styling Thickening Composition

The styling thickener was a commercially prepared polymeric dispersion manufactured by Seppic, Inc. under the trademark Sepigel 305. The formulation of the Sepigel material is shown below:

| Ingredient | % | CTFA Designation |
|---|---|---|
| Sepigel 305 | 100% | (Polyacrylamide (and) C13–14 Isoparaffin (and) Laureth-7) |

Additional similar technology from Seppic that would apply to this system is listed below:

| Ingredient | % | CTFA Designation |
|---|---|---|
| Sepigel 501 | 100% | (Acrylamides Copolymer (and) Mineral Oil (and) C13–14 Isoparaffin (and) Polysorbate 85) |

EXAMPLE 7

Shine Enhancing Additive

A shine additive composition was prepared by combining silicone-based fluids commercially available from Dow Corning. The formulation of the shine additive composition is shown below in TABLE 7. The ingredients are added to a dry, stainless vessel and mixed together with a prop mixer until uniform (15–30 minutes). The resulting composition is a clear, oily liquid.

TABLE 7

| Ingredient | % | CTFA Designation |
| --- | --- | --- |
| Dow Corning 344 Fluid | 28.57 | (Cyclomethicone) |
| Dow Corning 1401 Fluid | 57.14 | (Cyclomethicone, Dimethiconol) |
| Dow Corning 200 Fluid | 14.29 | (Dimethicone) |
|  | 100% |  |

EXAMPLE 8

Moisturizing Agent Composition

A moisturizing composition for inclusion in the shampoo, conditioner, or styling composition was prepared by combining together the ingredients shown below in TABLE 8, and mixing the ingredients in a dry, stainless vessel at about 150–200 rpm speed, at 25–30° C., for about 15–30 minutes. The composition was an amber colored, clear, low viscosity, oily liquid.

TABLE 8

| Ingredient | % | CTFA Designation |
| --- | --- | --- |
| Rice Bran | 80.00 | (Rice Bran Oil) |
| Meadowfoam Oil | 0.20 | (Meadowfoam Oil) |
| Evening Primrose Oil | 0.001 | (Evening Primrose Oil) |
| Olive Oil | 0.10 | (Olive Oil) |
| Captex 200 | 19.299 | (Propylene Glycol Dicaprylate/Dicaprate) |
| Emcon Copaiba | 0.10 | (Copaiba Oil) |
| Covitol 544 | 0.20 | (Tocopherol Acetate) |
| Aloe Vera Oil | 0.10 | (Aloe Vera Oil) |
|  | 100% |  |

EXAMPLE 9

Multi-Vitamin Additive

A multi-vitamin composition for inclusion in the shampoo, conditioner, or styling composition was prepared by combining together the ingredients shown in TABLE 9 using the following procedure:

Add water to a stainless vessel. Heat water to 65° C. At 65° C., add allantoin, wheat germamidopropalkonium chloride, panthenol, tetrasodium EDTA. Mix until uniform. Add sorbitol, dimethicone copolyol, and dicetyldimonium chloride. Mix until uniform. Premix vitamin A and $D_3$, tocopheryl acetate, and nonoxynol-10. Add mixture and mix until uniform (10–15 minutes). Cool batch to 25–30° C. At 25–30° C., add preservatives. Q.S. citric acid to pH 4.5–4.7. Mix until uniform, about 10–15 minutes. The resulting product is a water-thin, opaque liquid.

TABLE 9

| Ingredient | % | CTFA Designation |
| --- | --- | --- |
| Deionized Water | 94.15 | (Water) |
| Allantoin | 0.25 | (Allantoin) |
| Incroquat WG-85 | 0.25 | (Wheat Germamidopropalkonium Chloride) |
| Panthenol | 0.50 | (Panthenol) |
| Hampene 100S | 0.13 | (Tetrasodium EDTA) |
| Sorbitol 70% | 1.00 | (Sorbitol) |
| Dow Corning 193 Surfactant | 0.20 | (Dimethicone Copolyol) |
| Varisoft 432 CG | 2.00 | (Dicetyl Dimonium Chloride) |
| Vitamin A + D3 | 0.01 | (Corn Oil, Retinyl Palmitate, Cholecalciferol) |
| Covitol 544 | 0.01 | (Tocopherol Acetate) |
| Surfonic N-95 | 0.30 | (Nonoxynol-10) |
| Germaben II | 1.00 | (Propylene Glycol, Diazolidinyl Urea, Methylparaben, Propylparaben) |
| Glydant | 0.20 | (DMDM Hydantoin) |
| Citric Acid | O.S. | (Citric Acid) |
|  | 100% |  |

EXAMPLE 10

Animal-Derived Strengthening Agent

A strengthening agent made from animal-derived proteins was prepared by combining together the ingredients shown below in TABLE 10, and mixing the ingredients in a stainless vessel equipped with prop mixing at about 150–200 rpm speed, 25–30° C., for about 30–60 minutes. The resulting composition is a clear to slightly hazy, dark amber, water-thin liquid.

TABLE 10

| Ingredient | % | CTFA Designation |
| --- | --- | --- |
| Water | 69.70 | (Water) |
| Peptein 2000 | 30.00 | (Hydrolyzed Collagen) |
| Kathon CG | 0.30 | (Methylchloroisothiazolinone, |
|  | 100% | Methylisothiazolinone) |

EXAMPLE 12

Plant-Derived Strengthening Agent

A strengthening agent made of plant-derived proteins was prepared by combining together the ingredients shown below in TABLE 11, and mixing the ingredients in a stainless vessel equipped with prop mixing at about 150 rpm-200 rpm speed, 25–30° C., for about 30–60 minutes. The resulting composition is a clear to slightly hazy, light to dark amber, water-thin liquid.

TABLE 11

| Ingredient | % | CTFA Designation |
| --- | --- | --- |
| Water | 73.70 | (Water) |
| Vegequat W | 0.50 | (Hydroxypropyltrimonium Hydrolyzed Wheat Protein) |
| Crodasone W | 0.50 | (Hydrolyzed Wheat Protein Polysiloxane Copolymer) |
| Cropeptide W | 25.00 | (Hydrolyzed Wheat Protein and Wheat Oligosaccharides) |

TABLE 11-continued

| Ingredient | % | CTFA Designation |
|---|---|---|
| Kathon CG | 0.30 | (Methylchloroisothiazolinone, |
|  | 100% | Methylisothiazolinone) |

EXAMPLE 13

Stimulating or Astringent Herbal Additive

An herbal additive made of stimulating or astringent herbal extracts was prepared by combining together the ingredients shown below in TABLE 12, and mixing the ingredients in a stainless vessel equipped with prop mixing at about 150–200 rpm speed, 25–30° C., for about 30–60 minutes. The resulting composition is a clear, pale straw colored, water-thin liquid.

TABLE 12

| Ingredient | % | CTFA Designation |
|---|---|---|
| Deionized Water | 98.30 | (Water) |
| Actiphyte of Chamomile | 0.10 | (Matricaria Extract, Propylene Glycol, Water) |
| Phytelene of Cucumber | 0.10 | (Cucumber Extract, Propylene Glycol, Water) |
| Actiphyte of Kola Nut | 0.10 | (Kola Nut Extract, Propylene Glycol, Water) |
| Phytelene of Peppermint | 0.10 | (Peppermint Extract, Propylene Glycol, Water) |
| Extract of Basil | 0.10 | (Basil Extract, Propylene Glycol, Water) |
| Phytelene EG010 Sage | 0.10 | (Sage extract, Propylene Glycol, Water) |
| Germaben II | 1.00 | (Diazolidinyl Urea, Propylene Glycol, Methylparaben, Propylparaben) |
| Glydant | 0.10 | (DMDM Hydantoin) |
|  | 100% |  |

EXAMPLE 14

Soothing Herbal Additive

An herbal additive made of soothing herbal extracts was prepared by combining together the ingredients shown below in TABLE 13, and mixing the ingredients in a stainless vessel equipped with prop mixing at about 150–200 rpm speed, 25–30° C., for about 30–60 minutes. The resulting composition is a clear, pale straw colored, water-thin liquid.

TABLE 13

| Ingredient | % | CTFA Designation |
|---|---|---|
| Deionized Water | 97.90 | (Water) |
| Witch Hazel Extract | 0.10 | (Witch Hazel Extract, Propylene Glycol, Water) |
| Marigold Flower Extract | 0.10 | (Calendula Extract, Propylene Glycol, Water) |
| Sunflower Extract | 0.10 | (Sunflower Extract, Propylene Glycol, Water) |
| Covera | 0.50 | (Aloe Vera Gel) |
| Lavender Extract | 0.10 | (Lavender Extract, Propylene Glycol, Water) |
| Birch Leaves Extract | 0.10 | (Birch Leaves Extract, Propylene Glycol, Water) |

TABLE 13-continued

| Ingredient | % | CTFA Designation |
|---|---|---|
| Germaben II | 1.00 | (Diazolidinyl Urea, Propylene Glycol, Methylparaben, Propylparaben) |
| Glydant | 0.10 | (DMDM Hydantoin) |
|  | 100% |  |

EXAMPLE 15

Volumizing/Styling Composition

An optional volumizing/styling composition was prepared by combining the ingredients shown in TABLE 14, below following the procedure outlined below:

Add water to a stainless steel vessel equipped with a prop mixer. Add preservative to the water and mix for 15 minutes, or until uniform. The polyquaternium-11, and PVP/VA copolymer solutions are added with mixing. Mix for 30–60 minutes or until uniform.

The resulting product is a pale yellow, clear, low viscosity liquid.

TABLE 14

| Ingredient | % | CTFA Designation | Comments |
|---|---|---|---|
| Deionized Water | 75.0 | (Water) |  |
| Germaben II | 1.0 | (Propylene Glycol (and) Diazolidinyl Urea (and) Methylparaben (and) Propylparaben) |  |
| Gafquat 755N | 8.0 | (Polyquaternium-11) | 20% solution in water |
| PVP/VA W-735 | 16.0 | (PVP/VA Copolymer) | 50% solution in water |

EXAMPLE 16

Color Concentrates

Color concentrates were prepared for use in the shampoo, conditioner, and styling compositions according to the formulations shown below in TABLES 15–21. The concentrates were prepared by combining together the ingredients in the following manner:

Add water to a stainless vessel equipped with prop mixer and heating and cooling capabilities. Adjust mixing to 200–250 rpm. Heat to 60° C. At 60° C., add cetyl betaine, PEG-7 glyceryl cocoate, octoxynol-9, lauryl pyrrolidone, PEG-120 methyl glucose dioleate, and tetrasodium EDTA. Mix at 250–300 rpm for 30 minutes or until uniform. At 60° C., add appropriate dyes and mix at 250–300 rpm for 30 minutes or until uniform. Cool to 35° C. with mixing (250–300 rpm). Add potassium sorbate, and dimethyl hydroxymethyl pyrazole at 35° C. Mix for 15 minutes or until uniform. Adjust pH to 4.5 with citric acid.

The resulting composition is a hazy, low viscosity, brightly colored liquid.

TABLE 15

Orange Color Concentrate

| Ingredient | % | CTFA Designation |
|---|---|---|
| Deionized Water | 64.80 | (Water) |
| Detaine PB | 3.00 | (Cetyl Betaine) |
| Cetiol HE | 25.00 | (PEG-7 Glyceryl Cocoate) |
| Triton X-100 | 5.00 | (Octoxynol-9) |
| Surfadone LP-300 | 0.50 | (Lauryl Pyrrolidone) |
| Glucamate DOE-120 | 0.50 | (PEG-120 Methyl Glucose Dioleate) |
| Hampene 100S | 0.10 | (Tetrasodium EDTA) |
| Disperse Black 9 | 0.213 | (None) |
| Lowacryl Red 46 | 0.587 | (None) |
| Potassium Sorbate | 0.20 | (Potassium Sorbate) |
| Busan 1504 | 0.10 | (Dimethyl Hydroxymethyl Pyrazole) |
| Citric Acid | O.S. 100% | (Citric Acid) |

TABLE 16

Brown Color Concentrate

| Ingredient | % | CTFA Designation |
|---|---|---|
| Deionized Water | 63.20 | (Water) |
| Detaine PB | 3.00 | (Cetyl Betaine) |
| Cetiol HE | 25.00 | (PEG-7 Glyceryl Cocoate) |
| Triton X-100 | 5.00 | (Octoxynol-9) |
| Surfadone LP-300 | 0.50 | (Lauryl Pyrrolidone) |
| Glucamate DOE-120 | 0.50 | (PEG-120 Methyl Glucose Dioleate) |
| Hampene 100S | 0.10 | (Tetrasodium EDTA) |
| Lowadene Orange 3 | 1.20 | (None) |
| Disperse Black 9 | 0.60 | (None) |
| Lowadene Blue 62500 | 0.30 | (None) |
| Lowadene Violet #1 Conc. | 0.30 | (None) |
| Potassium Sorbate | 0.20 | (Potassium Sorbate) |
| Busan 1504 | 0.10 | (Dimethyl Hydroxymethyl Pyrazole) |
| Citric Acid | O.S. 100% | (Citric Acid) |

TABLE 17

Red Color Concentrate

| Ingredient | % | CTFA Designation |
|---|---|---|
| Deionized Water | 62.60 | (Water) |
| Detaine PB | 3.00 | (Cetyl Betaine) |
| Cetiol HE | 25.00 | (PEG-7 Glyceryl Cocoate) |
| Triton X-100 | 5.00 | (Octoxynol-9) |
| Surfadone LP-300 | 0.50 | (Lauryl Pyrrolidone) |
| Glucamate DOE-120 | 0.50 | (PEG-120 Methyl Glucose Dioleate) |
| Hampene 100S | 0.10 | (Tetrasodium EDTA) |
| Lowacryl Red 46 | 3.00 | (None) |
| Potassium Sorbate | 0.20 | (Potassium Sorbate) |
| Busan 1504 | 0.10 | (Dimethyl Hydroxymethyl Pyrazole) |
| Citric Acid | O.S. 100% | (Citric Acid) |

TABLE 18

Blue Color Concentrate

| Ingredient | % | CTFA Designation |
|---|---|---|
| Deionized Water | 63.19 | (Water) |
| Detaine PB | 3.00 | (Cetyl Betaine) |
| Cetiol HE | 25.00 | (PEG-7 Glyceryl Cocoate) |
| Triton X-100 | 5.00 | (Octoxynol-9) |
| Surfadone LP-300 | 0.50 | (Lauryl Pyrrolidone) |
| Glucamate DOE-120 | 0.50 | (PEG-120 Methyl Glucose Dioleate) |
| Hampene 100S | 0.10 | (Tetrasodium EDTA) |
| Lowadene Blue 62500 | 1.96 | (None) |
| Disperse Black 9 | 0.15 | (None) |
| Lowadene Violet #1 Conc. | 0.30 | (None) |
| Potassium Sorbate | 0.20 | (Potassium Sorbate) |
| Busan 1504 | 0.10 | (Dimethyl Hydroxymethyl Pyrazole) |
| Citric Acid | O.S. 100% | (Citric Acid) |

TABLE 19

Yellow Color Concentrate

| Ingredient | % | CTFA Designation |
|---|---|---|
| Deionized Water | 63.80 | (Water) |
| Detaine PB | 3.00 | (Cetyl Betaine) |
| Cetiol HE | 25.00 | (PEG-7 Glyceryl Cocoate) |
| Triton X-100 | 5.00 | (Octoxynol-9) |
| Surfadone LP-300 | 0.50 | (Lauryl Pyrrolidone) |
| Glucamate DOE-120 | 0.50 | (PEG-120 Methyl Glucose Dioleate) |
| Hampene 100S | 0.10 | (Tetrasodium EDTA) |
| Lowadene Orange 3 | 1.20 | (None) |
| Disperse Black 9 | 0.60 | (None) |
| Potassium Sorbate | 0.20 | (Potassium Sorbate) |
| Busan 1504 | 0.10 | (Dimethyl Hydroxymethyl Pyrazole) |
| Citric Acid | O.S. 100% | (Citric Acid) |

TABLE 20

Black Color Concentrate

| Ingredient | % | CTFA Designation |
|---|---|---|
| Deionized Water | 63.20 | (Water) |
| Detaine PB | 3.00 | (Cetyl Betaine) |
| Cetiol HE | 25.00 | (PEG-7 Glyceryl Cocoate) |
| Triton X-100 | 5.00 | (Octoxynol-9) |
| Surfadone LP-300 | 0.50 | (Lauryl Pyrrolidone) |
| Glucamate DOE-120 | 0.50 | (PEG-120 Methyl Glucose Dioleate) |
| Hampene 100S | 0.10 | (Tetrasodium EDTA) |
| Lowadene Blue 62500 | 1.33 | (None) |
| Lowadene Violet #1 Conc. | 0.27 | (None) |
| Lowadene Orange 3 | 0.80 | (None) |
| Potassium Sorbate | 0.20 | (Potassium Sorbate) |
| Busan 1504 | 0.10 | (Dimethyl Hydroxymethyl Pyrazole) |
| Citric Acid | O.S. 100% | (Citric Acid) |

TABLE 21

Violet Color Concentrate

| Ingredient | % | CTFA Designation |
|---|---|---|
| Deionized Water | 62.60 | (Water) |
| Detaine PB | 3.00 | (Cetyl Betaine) |
| Cetiol HE | 25.00 | (PEG-7 Glyceryl Cocoate) |
| Triton X-100 | 5.00 | (Octoxynol-9) |
| Surfadone LP-300 | 0.50 | (Lauryl Pyrrolidone) |
| Glucamate DOE-120 | 0.50 | (PEG-120 Methyl Glucose Dioleate) |
| Hampene 100S | 0.10 | (Tetrasodium EDTA) |
| Lowadene Violet #1 Conc. | 3.00 | (None) |
| Potassium Sorbate | 0.20 | (Potassium Sorbate) |
| Busan 1504 | 0.10 | (Dimethyl Hydroxymethyl Pyrazole) |
| Citric Acid | O.S. | (Citric Acid) |
| | 100% | |

Customized colors.

The color concentrates can be combined as follows to provide customized colors

| | | Ratio | Parts Per 100 Parts Base |
|---|---|---|---|
| Auburn: | Red Concentrate | 1 | 0.5 |
| | Brown Concentrate | 6 | 2.75 |
| Ash Brown: | Brown Concentrate | 5 | 2.25 |
| | Blue Concentrate | 1 | 0.90 |
| Golden Brown: | Brown Concentrate | 5 | 2.25 |
| | Yellow concentrate | 2 | 0.90 |

What is claimed is:

1. A system for use in preparing a customized conditioning composition, comprising:
   a first package containing an aqueous conditioner base; and
   a second package containing a conditioner thickener;
   the conditioner base having a viscosity of less than about 25 cps, and comprising about 1–8 wt-% quaternary ammonium salt; and
   the conditioner thickener being compatible with the conditioner base and comprising a water dispersible, oil based, cationic polymeric solution;
   wherein when the conditioner thickener is combined with the conditioner base to form the customized conditioning composition having a viscosity of about 10,000–150,000 cps.

2. The system of claim 1, further comprising at least one hair enhancing additive selected from the group consisting of shine enhancer, moisturizer, herbal additive, hair strengthening agent, vitamin additive, non-oxidative colorant, volumizing/styling agent wherein at least one enhancing additive is separately packaged from the first and second package.

3. The system of claim 1, wherein the quaternary ammonium salt in at least one of the conditioner base or the conditioner thickener is selected from the group consisting of cetrimonium chloride, steartrimonium chloride, polyquaternium, and mixtures thereof.

4. The system of claim 1, wherein the conditioner base further comprises about 0.5–1.5 wt-% solubilizing agent selected from the group consisting of a polyalkylene glycol ether of a $C_{12}$–$C_{18}$ fatty alcohol, a polyhydric alcohol, and mixtures thereof.

5. The system of claim 4, wherein the solubilizing agent is selected from the group consisting of isoceteth-20, isoceteareth-8-stearate, isoceteth-1-stearate, dimethyl isosorbide, cetereth-2, laureth-23, and mixtures thereof.

6. The system of claim 1, wherein the conditioner thickener and conditioner base are combined in a ratio of about 1.5:98.5 to about 3:97 and the resulting conditioner composition has a viscosity of about 10,000–50,000 cps about 1–2 hours after the conditioner thickener and conditioner base are combined.

7. The system of claim 1, wherein the conditioner thickener and conditioner base are combined in a ratio of about 4:96 to about 5:95 and the resulting conditioner composition has a viscosity of about 100,000–150,000 cps about 1–2 hours after the conditioner thickener and conditioner base are combined.

8. The system of claim 1, wherein the cationic polymeric solution comprises Salcare-96.

9. The method of claim 1, wherein the thickener comprises Sepigel-305.

10. The system of claim 1, wherein at least one of the base composition or the thickening composition comprise a minor but effective amount of a germicidal agent, an antioxidant, a chelating/sequestering agent, fragrance, or UV absorber.

11. The system of claim 1, packaged as an article of manufacture in combination with instructions for formulating the hair care system to produce the customized hair care product.

12. A method of preparing a customized conditioning composition, comprising:
    combining a first package containing an aqueous conditioner base having a first viscosity of less than about 25 cps and a second package containing a compatible liquid conditioner thickener having a second viscosity wherein the base composition comprises about 1–8 wt % quaternary ammonium salt; the conditioner thickener comprises a cationic polymeric solution; and the customized conditioning composition has a viscosity of about 10,000 cps to about 150,000 cps.

* * * * *